United States Patent
Stakenborg et al.

(10) Patent No.: US 11,276,003 B2
(45) Date of Patent: Mar. 15, 2022

(54) METHOD FOR WRITING DATA IN DNA BASED MEMORIES

(71) Applicant: IMEC vzw, Leuven (BE)

(72) Inventors: Tim Stakenborg, Heverlee (BE); Chang Chen, Heverlee (BE); Kris Covens, Kessel-Lo (BE); Qing Cai, Muizen (BE); Maarten Fauvart, Bertem (BE)

(73) Assignee: IMEC vzw, Leuven (BE)

( * ) Notice: Subject to any disclaimer, the term of this patent is extended or adjusted under 35 U.S.C. 154(b) by 450 days.

(21) Appl. No.: 16/224,496

(22) Filed: Dec. 18, 2018

(65) Prior Publication Data
US 2019/0205768 A1    Jul. 4, 2019

(30) Foreign Application Priority Data
Dec. 29, 2017   (EP) ..................................... 17211093

(51) Int. Cl.
*G06N 3/12*   (2006.01)
*G11C 11/00*  (2006.01)
(Continued)

(52) U.S. Cl.
CPC .............. *G06N 3/123* (2013.01); *B82Y 10/00* (2013.01); *C12N 15/10* (2013.01); *G11C 11/00* (2013.01);
(Continued)

(58) Field of Classification Search
CPC ........ G06N 3/123; C12N 15/10; G16B 30/00; B82Y 10/00; G11C 11/00; G11C 13/0016; G11C 13/00019
See application file for complete search history.

(56) References Cited

U.S. PATENT DOCUMENTS

| 8,771,491 B2 * | 7/2014 | Huber .................. C12Q 1/6869 204/452 |
| 10,934,585 B2 * | 3/2021 | Pham .................. C12Q 1/6874 |

(Continued)

OTHER PUBLICATIONS

S. M. H. T. Yazdi, H. M. Kiah, E. Garcia-Ruiz, J. Ma, H. Zhao and O. Milenkovic, "DNA-Based Storage: Trends and Methods," in IEEE Transactions on Molecular, Biological and Multi-Scale Communications, vol. 1, No. 3, pp. 230-248, Sep. 2015, doi: 10.1109/TMBMC.2016.2537305. (Year: 2015).*

(Continued)

*Primary Examiner* — Ajay Ojha
(74) *Attorney, Agent, or Firm* — Knobbe Martens Olson & Bear LLP

(57) ABSTRACT

A method for writing data including a sequence of bits, the data being written in a form of DNA, by in-vitro enzymatically producing memory DNA from a strand of memory writing substrate DNA is disclosed. In one aspect, the method includes repeating of: receiving a sub-sequence of the sequence of bits, the sub-sequence including at least one bit; selecting memory nucleotides based on the sub-sequence; contacting, in liquid medium including the strand of memory writing substrate DNA contacted with an enzyme, the selected memory nucleotides and the enzyme; and synthesizing a portion of the memory DNA from a portion of the strand of memory writing substrate DNA by the enzyme and at least one of the memory nucleotides of the solution, thereby producing memory DNA including memory nucleotides corresponding to bits of the sequence of bits. The disclosed technology further relates to a microfluidic system including a microfluidic chip and a controller.

14 Claims, 2 Drawing Sheets

Specification includes a Sequence Listing.

(51) Int. Cl.
*G16B 30/00* (2019.01)
*B82Y 10/00* (2011.01)
*C12N 15/10* (2006.01)
*G11C 13/00* (2006.01)

(52) U.S. Cl.
CPC ...... *G11C 13/0016* (2013.01); *G11C 13/0019* (2013.01); *G16B 30/00* (2019.02)

(56) References Cited

U.S. PATENT DOCUMENTS

| | | | |
|---|---|---|---|
| 2003/0228611 A1 | 12/2003 | Chruch et al. | |
| 2005/0053968 A1* | 3/2005 | Bharadwaj | G16B 30/00 435/6.12 |
| 2005/0221333 A1* | 10/2005 | Sundararajan | C12Q 1/6869 435/6.19 |
| 2016/0358055 A1 | 12/2016 | Church | |
| 2019/0291106 A1* | 9/2019 | Jans | B01L 3/502715 |

OTHER PUBLICATIONS

Limbachiya Dixita, Gupta K Manish, 2015. Natural Data Storage: A Review on Sending Information from Now to Then ACM J. Emerg. Technol. Comput. Syst. V, N, Article A (Jan. YYYY), 17 pages. DOI:http://dx.doi.org/10.1145/0000000.0000000 (Year: 2015).*
M. Sarkar and P. Ghosal, "Implementing Data Structure Using DNA: An Alternative in Post CMOS Computing," 2015 IEEE Computer Society Annual Symposium on VLSI, Montpellier, France, 2015, pp. 345-349, doi: 10.1109/ISVLSI.2015.106. (Year: 2015).*
Extended Search Report issued in European Patent Application No. 17211093.4, dated Jun. 27, 2018.

* cited by examiner

__US 11,276,003 B2__

METHOD FOR WRITING DATA IN DNA BASED MEMORIES

CROSS-REFERENCE TO RELATED APPLICATIONS

This application claims priority to European Patent Application No. 17211093.4, filed Dec. 29, 2017, the content of which is incorporated by reference herein in its entirety.

REFERENCE TO SEQUENCE LISTING

The present application is being filed along with a Sequence Listing in electronic format. The Sequence Listing is provided as a file entitled SequenceListing, created Dec. 18, 2018, which is approximately 386 bytes in size. The information in the electronic format of the Sequence Listing is incorporated herein by reference.

BACKGROUND

Field

The disclosed technology relates to a method for writing data.

Description of the Related Technology

There exists a data storage problem resulting from very large amounts of data being generated each year, for example in the form of graphics and text. All data being generated can not be captured using present storage equipment including hard drives, disks and tapes.

DNA has been proposed for storage of data, and it has been suggested that, in theory, it may be possible to store 215 petabytes in a single gram of DNA. Although it is known to store digital data in DNA, known methods are inefficient compared to theoretical storage capacity of DNA. Further, known methods suffer from a high costs per byte, and low speed of writing the data on the DNA. Further, known methods suffer from high error rates in the writing of data.

Thus, there is a need for rapid and cost efficient methods of storing data on DNA with low error frequency.

SUMMARY OF CERTAIN INVENTIVE ASPECTS

An objective of at least some aspects of the present inventive concept is to overcome one or more problems related to prior art.

According to one aspect, there is provided a method for writing data comprising a sequence of bits, the data being written in a form of DNA, by in-vitro enzymatically producing memory DNA from a strand of memory writing substrate DNA, the method comprising: repeating of: receiving a sub-sequence of the sequence of bits, the sub-sequence comprising at least one bit; selecting memory nucleotides based on the sub-sequence; contacting, in liquid medium comprising the strand of memory writing substrate DNA contacted with an enzyme, the selected memory nucleotides and the enzyme; and synthesising a portion of the memory DNA from a portion of the strand of memory writing substrate DNA by the enzyme and at least one of the memory nucleotides of the solution, thereby producing memory DNA comprising memory nucleotides corresponding to bits of the sequence of bits.

The method provides for writing and storing of data and bits on a string of DNA.

The in-vitro enzymatically producing memory DNA allow for rapid writing of data with low error frequency obtainable with an enzyme in a controlled in-vitro environment. The use of enzyme, further provides for improved synthesis compared to, for example, synthesis based on phosphoramidite chemistry.

The receiving a sub-sequence of the sequence of bits, enables writing of the received sub-sequence. Selecting memory nucleotides based on the sub-sequence allows for selecting memory nucleotides which corresponds to the received sub-sequence. Further, the memory nucleotide may be selected for pairing with a base of the strand of memory writing substrate DNA.

The contacting the selected memory nucleotides and the enzyme is an efficient way of allowing synthesis by the enzyme and, thus, allowing writing of memory DNA.

The contacting taking place in liquid medium comprising the strand of memory writing substrate DNA contacted with an enzyme, may be in a microfluidic channel or compartment, for example on a microfluidic chip.

Synthesising a portion of the memory DNA from a portion of the strand of memory writing substrate DNA by the enzyme and at least one of the memory nucleotides of the solution, allows for a portion of memory writing DNA to be produced, which portion of memory DNA comprises memory nucleotide corresponding to a received sub-sequence of the sequence of bits. The repeating of the method allows for the data sequence to be written and stored as memory DNA.

Writing data on DNA as described by the method, allows for large data sequences to be stored at least in part due to the large size DNA can take.

The strand of memory writing substrate DNA may be present in form of a double strand DNA. Thereby, the substrate DNA may be stable over long periods and efficiently handled and stored. Yet further, the substrate DNA is suitable for writing using a plurality of different enzymes.

The repeating may be performed, for example, on a microfluidic chip or microfluidic device.

The contacting may be by introducing a solution of memory nucleotides to a solution comprising the strand of memory writing substrate DNA. The contacting may be performed on a microfluidic chip or microfluidic device by flowing a solution of memory nucleotides into a compartment or microfluidic channel on the chip or microfluidic device comprising the strand of memory writing substrate DNA.

The strand of memory writing substrate DNA may have a predetermined or known sequence. The memory nucleotides, further, may be selected for base pairing with bases of the portion of the strand of memory writing substrate DNA.

A predetermined or known sequence of the memory writing substrate DNA allows for efficient selection of memory nucleotides for synthesis. Further, the known sequence may be used for addressing predetermined portions or bases of the memory writing substrate DNA. The predetermined sequence may be taken advantage of by, for a specific repetition of the method, selecting memory nucleotides which not only corresponds to or is based on a received bit, but also pairs with one or more bases of the portion of the memory writing substrate DNA.

The receiving a sub-sequence of the sequence of bits, for each repeating, may be performed sequentially from the sequence of bits, and the memory DNA thereby may comprise memory nucleotides corresponding to the data by having the same sequential order as the bits of the sub-sequence and the sequence of bits.

The selecting of memory nucleotides may comprise: selecting a memory nucleotide comprising a first label or first modification on a condition that the sub-sequence comprises a predetermined first sequence of bit-values, or selecting a memory nucleotide comprising a second label or second modification on a condition that the sub-sequence comprises a predetermined second sequence of bit-values.

Thereby, a memory nucleotide may correspond to a sequence of bits, or a single bit. It will be understood that the method allows that not just one bit at the time to be received and written, but 1, 2, 3, 4, or more, bits at a time and allowing one label or modification to correspond to the sub-sequence of bits. Thus, rapid data writing and high bit-density on the memory DNA may be realised.

The first and second labels or modifications may, for example, correspond to zeros and ones, respectively. Labels or modifications may also, for example, correspond to a sequence of bits comprising 2, 3, 4, or more bits. To mention a few examples, a label may correspond to the predetermined sequence of 0,1,0; or 1,0; or 1110.

The portion of the strand of memory writing substrate DNA may comprises a single base, or a plurality of bases. Further, the receiving a sub-sequence may be receiving a plurality of bits. If the received sub-sequence comprises a plurality of identical bits, such as, for example, a plurality of adjacent zeros, the adjacent bits may be written using memory nucleotide with one type of label or modification corresponding to the identical bits until all bits of the sub-sequence are written on the memory DNA. As one alternative, only one memory nucleotide may be used if labelled or modified to correspond to the sub-sequence of bits comprising a plurality of bits.

The first and second labels may be selected from the group consisting of fluorescent dyes, functional groups, bulky or sterically differentiating groups. The functional groups may be selected from the group consisting of biotin, azide-, carboxy-, thiol-, epoxy-moieties, and the bulky or sterically differentiating groups may be selected from polyethylene glycol units of different length. Such groups are identifyable, and suitable for corresponding to the sub-sequence of the sequence of bits and differentiates bit-related monomers of the memory DNA from monomers unrelated to bits or related to different bits. Reading the memory DNA may be realised by different methods and be based on the memory nucleotides, labels or modifications.

The first or second modification may be a chemical group or functionality selected from the group consisting of biotin, azide-, carboxy-, thiol-, epoxy-moieties for post-synthesising labelling of the memory nucleotide with the first or second label respectively. Such groups may efficiently be provided with labels post synthesis. The may also be used as labels without further modification.

According to an alternative to the methods related to memory nucleotides comprising labels or modifications, the portion of the strand of memory writing substrate DNA may comprise base analogues capable of pairing with more than one type of base, thereby capable of synthesising using memory nucleotides having different bases.

Thereby, based on the received sub-sequence of the sequence of bits, a memory nucleotide with a base selected to correspond to that sub-sequence may be selected. The base sequence of the produced memory DNA thereby corresponds or relates to the sequence of bits.

The memory nucleotides may be selected from nucleotides comprising base A or base C, and the portion of the strand of memory writing substrate DNA may comprise an 8-oxodG or inosine group. The 8-oxodG base of DNA is capable of pairing with both A and C bases, thereby, dependent on the received sub-sequence of bits, either an A or a C may be incorporated with the memory DNA.

The selecting of memory nucleotides may comprise: selecting base A on a condition that the sub-sequence comprises a predetermined first sequence of bit-values, and selecting base C on a condition that the sub-sequence comprises a predetermined second bit-sequence.

The sub-sequence of the sequence of bits may consist of one bit, the memory nucleotides may be selected from nucleotides comprising base A or base C, and the portion of the strand of memory writing substrate DNA may comprise an 8-oxodG or inosine group, and the selecting of memory nucleotides may comprise: selecting base A on a condition that the sub-sequence consists of 0 or 1, and selecting base C on a condition that the sub-sequence consists of the other of 0 or 1.

Before or after a repeating of the method, a void portion of memory DNA which does not comprise memory nucleotides and therefore does not correspond to bits may be synthesised and incorporated with the memory DNA. For example, such void memory DNA may be synthesised between writing of A or C or labelled nucleotides.

Base A and base C may correspond to, for example, a bit value of 0 or a 1, respectively, or other predetermined sequence of bit values.

The portion of the strand of memory writing substrate DNA may comprise a plurality of adjacent 8-oxodG or inosine groups.

The method may further comprise, after the synthesising, halting the synthesising. Thereby, memory nucleotides which have been used in a repeating, may be removed from contact with the substrate DNA, such as by being flushed away from a synthesis compartment. The method thereby may be prepared for a repeating comprising synthesis with other memory nucleotides based on other received sub-sequence of the sequence of bits.

The portion of the strand of memory writing substrate DNA may comprise cleavable chain terminators or reversible nucleic acid binders, wherein the halting the synthesising is realised by the cleavable chain terminators or reversible nucleic acid binders. Such terminators or binders provide barriers on the DNA, which barriers the enzyme cannot proceed beyond without removing or disintegrating the barriers.

The method may further comprise, prior to the synthesising: cleaving the cleavable chain terminator, or unbinding of the reversible nucleic acid binders, thereby allowing initiating synthesising.

The cleaving or unbinding may be prior to the synthesising and following the contacting.

The reversible nucleic acid binder may be selected from, for example, suitable DNA binding proteins and short oligonucleotide probes.

The cleaving the cleavable chain terminator may be photo or electrically induced cleaving.

As one alternative to halting realised by the cleavable chain terminators or reversible nucleic acid binders, the halting the synthesis may be realised by deactivation of the enzyme by adjusting synthesis conditions in vicinity of the portion of the strand of memory writing substrate DNA, preferably by adjusting ion concentration and/or temperature, thereby halting or slowing down the synthesis and the method further comprising, prior to the synthesising, -activating the enzyme by adjusting synthesis conditions in vicinity of the portion of the strand of memory writing substrate DNA, by adjusting ion concentration and/or by adjusting temperature, thereby initiating synthesising.

Enzymes used for the synthesising may be deactivated or activated in a temperature interval or within concentration ranges of present ions.

The adjusting ion concentration, may be adjusting concentration of ions needed by the enzyme for synthesis. Increasing concentration of such ions may activate a deactivated enzyme, and vice versa.

The halting the synthesising may be realised by the next downstream base on strand of memory writing substrate DNA not being compatible with the base of the present selected memory nucleotide.

The enzyme may be selected from the group consisting of polymerases, reverse transcriptases, and RNA polymerases.

The enzyme may be a polymerase.

The strand of memory writing substrate DNA may be present together with a complementary strand of DNA.

Thereby the strand of memory writing substrate DNA may be stable over long periods.

The produced memory DNA may comprise a strand of DNA having memory nucleotides corresponding to the bits and having the same sequence as the bits of the sequence of bits.

The method may further comprise receiving the data to be written to the DNA.

According to another aspect there is provided a microfluidic system comprising a microfluidic chip and a controller. The microfluidic chip comprises a memory DNA synthesis compartment configured to comprise a strand of memory writing substrate DNA contacted with an enzyme in liquid, microfluidic channels fluidically connected with the memory DNA synthesis compartment and configured to forward liquids to the memory DNA synthesis compartment, memory nucleotide compartments, each fluidically connected to the memory DNA synthesis compartment via one of the microfluidic channels, and configured to comprise a solution of memory nucleotides, and wherein the controller is configured to repeatedly perform: receiving a sub-sequence of the sequence of bits, the sub-sequence comprising at least one bit; selecting memory nucleotides based on the sub-sequence; forwarding a solution comprising the selected memory nucleotides via one of the microfluidic channels to the memory DNA synthesis compartment, thereby providing contact between the selected memory nucleotides and the enzyme; and synthesising a portion of memory DNA from a portion of the strand of memory writing substrate DNA by the enzyme and at least one of the memory nucleotides of the solution, thereby producing memory DNA comprising memory nucleotides corresponding to bits of the sequence of bits.

This aspect may generally present the same or corresponding advantages as the former aspect.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION OF CERTAIN ILLUSTRATIVE EMBODIMENTS

With the present method, data in the form of a sequence of bits may be written in the form of memory DNA having, for example, labels or bases corresponding to the bits. The data is not limited to any particular data, but may be any form of data in the form of bits such as data files and obtained from any suitable data source such as, for example, a computer or computer memory, a memory disk, an instrument providing data, and data storage. The data source may be connected or linked directly or indirectly to the system implementing the method, thereby allowing bits to be received by the method and written in the form of memory DNA.

The labels or functionalities or type of nucleotide bases on the memory DNA, originating from memory nucleotides, function in denoting bits. The use of enzyme allows for rapid data writing and low error rates. The method comprises receiving a sub-sequence of bits from a sequence of bits to be written, and the enzyme is involved in writing the data by synthesising memory DNA using memory nucleotides corresponding to received bits. The method allows for, after several cycles, memory DNA being produced having bits incorporated as, for example, labels in the same sequential order as the sequence of bits of the data.

As used herein, bases A, C, G, and T, refers to Adenine, Cytosine, Guanine, and Thymine. Further, 8-oxodG refers to 8-hydroxydeoxyguanosine.

Figure 1:
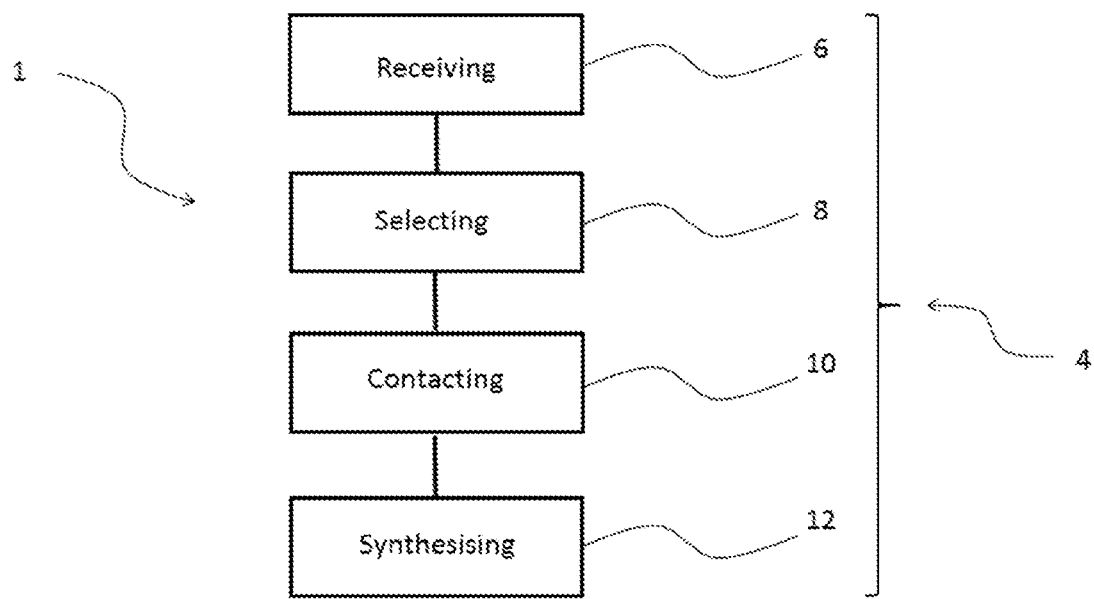
FIG. 1 is an illustration of a method according to an aspect.

With reference to FIG. 1, a method 1 for writing data comprising a sequence of bits, the data being written in a form of DNA, by in-vitro enzymatically producing memory DNA from a strand of memory writing substrate DNA, will now be described. The method 1 comprises repeating 4 of: receiving 6 a sub-sequence of the sequence of bits, the sub-sequence comprising at least one bit; selecting 8 memory nucleotides based on the sub-sequence; contacting 10, in liquid medium comprising the strand of memory writing substrate DNA contacted with an enzyme, the selected memory nucleotides and the enzyme; and synthesising 12 a portion of the memory DNA from a portion of the strand of memory writing substrate DNA by the enzyme and at least one of the memory nucleotides of the solution, thereby producing memory DNA comprising memory nucleotides corresponding to bits of the sequence of bits.

The repeating may proceed until deciding that the writing of data has come to an end, or until all data to be written has been written.

Figure 2:
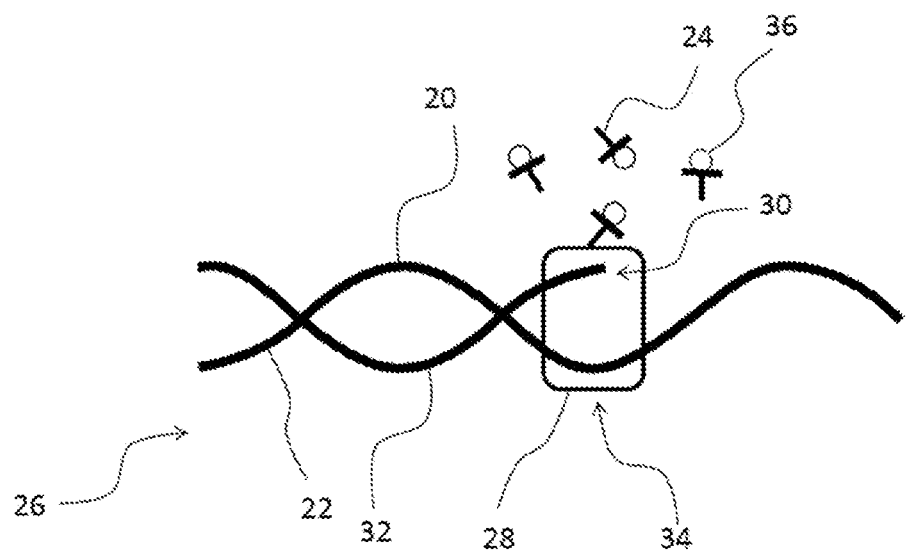
FIG. 2 is an illustration relating to a method according to an embodiment.

With reference to FIG. 2, a method 1 for writing data comprising a sequence of bits, the data being written in a form of DNA, by in-vitro enzymatically producing memory DNA from a strand 20 of memory writing substrate DNA 22 will now be further described. Base-pairs are not illustrated. The method 1 comprises repeating 4 of: receiving 6 a sub-sequence of the sequence of bits, the sub-sequence comprising at least one bit; selecting 8 memory nucleotides 24 based on the sub-sequence; contacting 10, in liquid medium 26 comprising the strand 20 of memory writing substrate DNA 22 contacted with an enzyme 28, the selected memory nucleotides 24 and the enzyme 28; and synthesising 12 a portion 30 of the memory DNA 32 from a portion 34 of the strand of memory writing substrate DNA 22 by the enzyme 28 and at least one of the memory nucleotides 24 of the solution 26, thereby producing memory DNA 32 comprising memory nucleotides 24 corresponding to bits of the sequence of bits.

With the method described with reference to FIG. 2, the memory nucleotides 24 have been illustrated comprising a circular shape 36. The circular shape 36 is intended to schematically illustrating that memory nucleotides 24 are selected based on the received sub-sequence, and that it corresponds to the sub-sequence. For example, the memory nucleotides 24 may comprise a first label or first modification, or a second label or second modification. The memory nucleotides 24 may further comprise additional labels or modifications, such as third, fourth, and fifth label or third, fourth, and fifth modification. The first and second label or first and second modification may, for example, correspond to one of 0 and 1, respectively and wherein the first and the second label or first and second modification does not correspond to the same bit-value. The first and second labels may each further correspond to a sub-sequence of bits comprising more than one bit. Additional labels or modifications may be used, for example, third, fourth, fifth, and sixth labels or modifications. Thereby, sub-sequences comprising several bits may be written at one time, or during one repeating. For example, it may be determined that a first, second, third, and fourth labels corresponds to predetermined sequence of bit-values of 0,0; 0,1; 1,0; 1,1, respectively. Thereby, by using four different labels, or modifications, the method may be performed wherein two bits may be received per repeating. The selecting of memory nucleotides 24 for such example may for example comprise: selecting a memory nucleotide comprising a first label or first modification on a condition that the sub-sequence comprises a predetermined first sequence of bit-values, for example, 0,0, selecting a memory nucleotide comprising a second label or second modification on a condition that the sub-sequence comprises a predetermined second sequence of bit-values, for example 0,1, selecting a memory nucleotide comprising a third label or third modification on a condition that the sub-sequence comprises a predetermined third sequence of bit-values, for example, 1,0, and selecting a memory nucleotide comprising a fourth label or fourth modification on a condition that the sub-sequence comprises a predetermined fourth sequence of bit-values, for example 1,1.

In addition to selecting labels for the memory nucleotides 24, the base of the memory nucleotides 24 may be selected for pairing with a base of the portion 34 of memory writing substrate DNA 22. Although, alternatively, a plurality of memory nucleotides 24 may be selected to comprise different bases, such that pairing will be realised.

Synthesising will follow in the repeating involving the selected memory nucleotide, the enzyme 28 and the portion 34 of the strand of memory writing substrate DNA. A known or predetermined base sequence of the strand of memory writing substrate DNA will allow efficient selection of memory nucleotides 24 with respect to bases for pairing with the substrate DNA.

The selecting of memory nucleotides 24 may comprise: selecting a memory nucleotide comprising a first label or first modification on a condition that the sub-sequence comprises a predetermined first sequence of bit-values, or selecting a memory nucleotide comprising a second label or second modification on a condition that the sub-sequence comprises a predetermined second sequence of bit-values.

Thus, the strand of memory writing substrate DNA 22 may have a predetermined or known sequence. Thereby, for example, the memory nucleotides 24 may further be selected to allow base pairing with the base of the portion 34 of the strand of memory writing substrate DNA 22.

The method may be performed on a microfluidic device or chip.

The receiving sub-sequence for each repeating may be performed sequentially from the sequence of bits, and the memory DNA thereby comprises memory nucleotides 24 in the same sequential order as the bits of the sequence of bits. Thereby, the memory DNA corresponds to the data being written.

The first and second labels may be selected from the group consisting of fluorescent dyes, functional groups, bulky or sterically differentiating groups, wherein the functional groups may be selected from the group consisting of biotin, azide-, carboxy-, thiol-, epoxy-moieties, and wherein the bulky or sterically differentiating groups may be selected from poly-ethylene glycol units of different length. The first or second modification may be a chemical group or functionality selected from the group consisting of biotin, azide-, carboxy-, thiol-, epoxy-moieties for post-synthesising labelling of the memory nucleotide, for example with the first or second label respectively.

Thereby, the memory nucleotides 24 may be selected to differ from each other if they correspond to different sub-sequences of bits, such as, for example, a one or zero. In addition, they differ from unlabelled or unmodified nucleotides. Thereby, it is clear which nucleotides of a memory DNA corresponds to written data and which are not related to data or bits. Reading may be realised by a plurality of methods.

The portion 34 of the strand of memory writing substrate DNA 22 may comprise base analogues capable of pairing with more than one type of base, thereby capable of synthesising using memory nucleotides 24 having different bases. Thereby, as an alternative to incorporate labelled or modified nucleotides, the memory nucleotides 24 may be selected wherein the base of the memory nucleotides 24 denotes or correlates with the received sub-sequence of bits.

It may be predetermined which type of base, incorporated with the memory nucleotides 24, corresponds to which sub-sequence of bits, for example 0, or 1.

Thus, instead of using, for example, labelled nucleotides, template-free or substrate or template-relaxed incorporation of standard nucleotides may be used. According to such embodiments, the incorporated memory nucleotides 24 are not determined by the enzyme 28, but may be determined by the design of the strand of memory writing substrate DNA 22 in combination with fluidic provision of the memory nucleotide nucleotides. Examples include, for example, memory writing substrate DNA comprising inosine or 8-oxodG.

Figure 3:
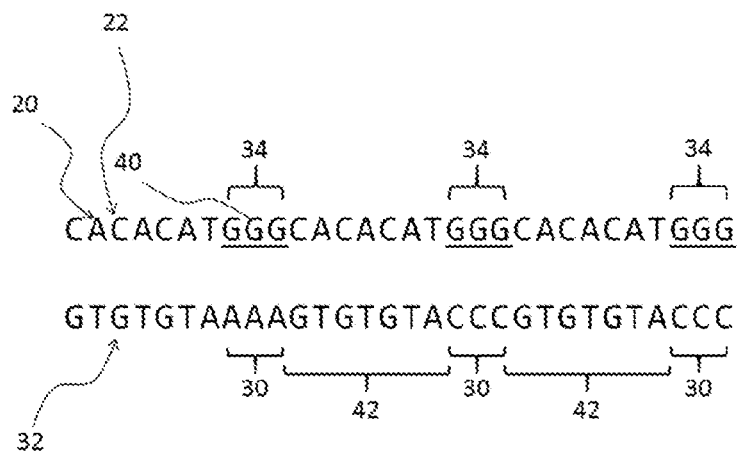
FIG. 3 is an illustration relating to a method according to an embodiment.

With reference to FIG. 3, one example using bases corresponding to bits will be discussed, which example takes advantage of the strand 20 of memory writing substrate DNA 22 comprises 8-oxodG, and particularly that the portion 34 of the strand 20 of memory writing substrate DNA 22 comprises an 8-oxodG. It will be appreciated that 8-oxodG may pair with either base A or base C. Thus, the memory nucleotides 24 may be selected from nucleotides comprising base A or base C, and the portion 34 of the strand of memory writing substrate DNA may comprise an 8-oxodG. With reference to FIG. 3, a method 1 for writing data comprising a sequence of bits, the data being written in a form of DNA, by in-vitro enzymatically producing memory DNA 32 from a strand 20 of memory writing substrate DNA 22 comprising 8-oxodG, will now be further described. In FIG. 3, an 8-oxodG group 40 is illustrated with an underlined G. The method 1 comprises repeating 4 of: receiving 6 a sub-sequence of the sequence of bits, the sub-sequence comprising at least one bit; selecting 8 memory nucleotides 24 based on the sub-section, from memory nucleotides 24 comprising base A or base C; contacting 10, in liquid medium 26 comprising the strand 20 of memory writing substrate DNA 22 contacted with an enzyme 28 (enzyme not illustrated), the selected memory nucleotides 24 and the enzyme 28; and synthesising 12 a portion 30 of the memory DNA 32 from a portion 34 of the strand of memory writing substrate DNA 22 by the enzyme 28 and at least one of the memory nucleotides 24 of the solution 26, thereby producing memory DNA 32 comprising memory nucleotides 24 corresponding to bits of the sequence of bits. The enzyme 28 may be, for example, Pol IV polymerase, which enzyme during the synthesising is able to incorporate either C or A, depending on which memory nucleotide has been selected based on the received sub-sequence. It is noted that in between portions 30 of the memory DNA 32, spacer DNA 42 has been introduced. The spacer DNA 42 does not correspond to bits or data according to the embodiment.

The selecting of memory nucleotides 24 may comprise: selecting base A on a condition that the sub-sequence comprises a predetermined first sequence of bit-values, and selecting base C on a condition that the sub-sequence comprises a predetermined second bit-sequence.

In the example, the strand of memory writing substrate DNA comprises a plurality of adjacent 8-oxodG or inosine groups. The memory writing substrate DNA 22 may have a predetermined sequence of bases having a design which does not allow writing of spacer DNA 42 having the same sequence as the portions 30 of the memory DNA 32, thereby allowing post writing differentiating between bit correlating bases and non-bit relating bases.

The site-specific modulation of the enzymes by, for example, local control of temperature or of ion-concentrations may be used for specifying which portion 34 of the memory writing substrate DNA being incorporated in the synthesising. Alternatively, a chain terminator can be used to locally allow the polymerase to continue incorporation of nucleotides after site-specific cleavage of the terminator.

According to an alternative to the example described with reference to FIG. 3, a memory writing substrate DNA comprising inosine or other DNA analogs may be used to incorporate different nucleotides.

Further, the enzyme, for example a suitable type of polymerase, may not be fully selective to base-complementarity, thus allowing incorporation of different nucleotides.

The method according to embodiments may further comprise, after the synthesising, halting the synthesising. Thereby, memory nucleotides 24 which have been used in a repeating, may be removed from contact with the substrate DNA. The method, thereby, may be prepared for a repeating comprising synthesis with other memory nucleotides 24 based on other received sub-sequence of the sequence of bits. For example if the memory nucleotides 24 comprise a first label or first modification, or a second label or second modification which is not suitable for the next repeating, and/or if the memory nucleotides 24 comprise a base which is not suitable for the next repeating, the memory nucleotides 24 may, thus, efficiently be removed from contact with the enzyme 28 after the halting. With the example discussed with reference to FIG. 3 and 8-oxodG, memory nucleotides 24 comprising base A or C may be removed from contact with the enzyme 28, and new nucleotides may be selected.

The portion 34 of the strand of memory writing substrate DNA may comprise cleavable chain terminators or reversible nucleic acid binders, wherein the halting the synthesising is realised by the cleavable chain terminators or reversible nucleic acid binders. Such terminators or binders may halt the enzyme in their capacity as acting as physical barriers on the memory writing substrate DNA. The method may further comprise, prior to the synthesising: cleaving the cleavable chain terminator, or unbinding of the reversible nucleic acid binders, thereby allowing initiating synthesising.

The cleaving or unbinding may be prior to the synthesising and following the contacting.

The reversible nucleic acid binder may be selected from, for example, suitable DNA binding proteins and short oligonucleotide probes.

The cleaving the cleavable chain terminator may be photo or electrically induced cleaving.

The halting the synthesising may be realised by deactivation of the enzyme by adjusting synthesis conditions in vicinity of the portion of the strand of memory writing substrate DNA, preferably by adjusting ion concentration and/or temperature, thereby halting or slowing down the synthesis and the method may further comprise, prior to the synthesising, activating the enzyme by adjusting synthesis conditions in vicinity of the portion of the strand of memory writing substrate DNA, by adjusting ion concentration and/or by adjusting temperature, thereby initiating synthesising.

The halting the synthesising may be realised by the next downstream base on strand of memory writing substrate DNA not being compatible with the base of the selected memory nucleotide. Activation, after such a halting, may be realised by providing nucleotides having a base compatible with the downstream base on the substrate DNA.

The halting and/or activating the enzyme may be conducted at specific positions of memory writing substrate DNA, thereby allowing determining the position where writing is terminated and/or initiated. A plurality of memory writing substrate DNA may, for example, be provided on a microfluidic device or arrangement, For example, an array of a plurality of memory writing substrate DNA may be used.

The adjusting of ion concentration, may be adjusting concentration of ions needed by the enzyme for synthesis. Such adjusting may be by providing liquids comprising suitable concentrations of the ions to the synthesising, such as to a synthesising compartment of a microfluidic arrangement via a microfluidic channel.

The enzyme may be selected from the group consisting of polymerases, reverse transcriptases, and RNA polymerases.

The enzyme may be a polymerase.

The strand of memory writing substrate DNA may present together with a complementary strand of DNA.

The produced memory DNA 32 may comprise a strand of DNA having memory nucleotides 24 corresponding to and having the same sequence as the bits of the sequence of bits.

Between repetitions, DNA may be synthesised with nucleotides which does not correspond to bits. Thereby, for example, spacer portions of DNA may be produced between bit-related bases of the DNA.

Figure 4:
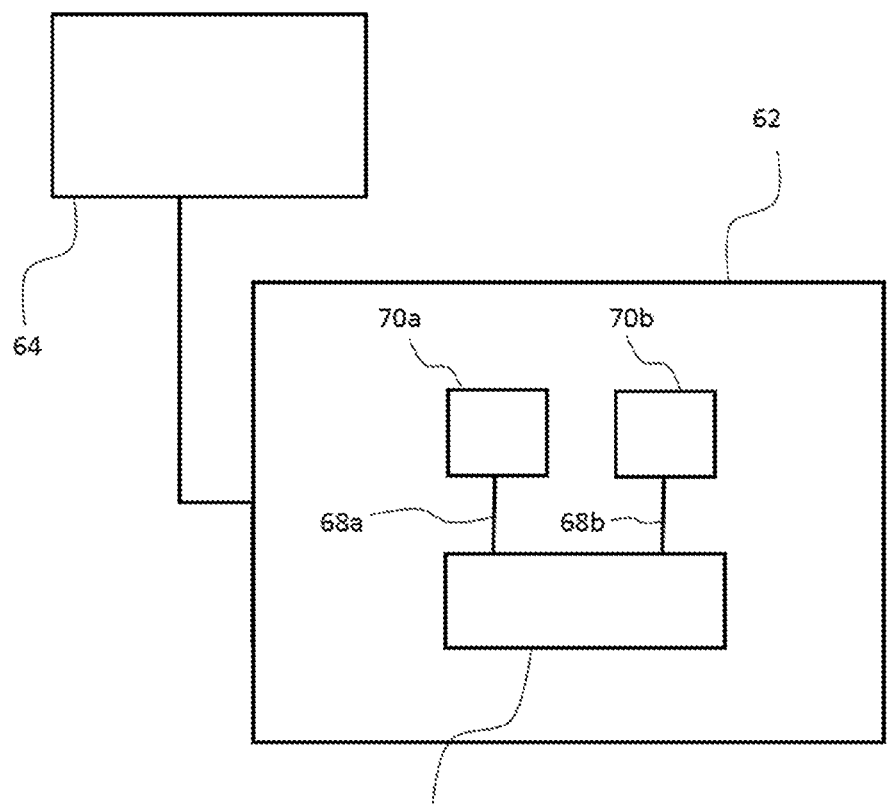
FIG. 4 is an illustration of a micro-fluidic system according to an embodiment.

With reference to FIG. 4, a micro-fluidic system 60 will now be discussed. The microfluidic system comprises a microfluidic chip 62 and a controller 64. The microfluidic chip 62 comprises a memory DNA 32 synthesis compartment 66, which may be for example a well, a compartment, or other suitable type of container, configured to comprise a strand of memory writing substrate DNA (not illustrated in FIG. 4) contacted with an enzyme 28 (not illustrated in FIG. 4) in liquid, microfluidic channels 68a,b fluidically connected with the memory DNA 32 synthesis compartment 66 and configured to forward liquids to the memory DNA 32 synthesis compartment, memory nucleotide compartments 70a,b, each fluidically connected to the memory DNA 32 synthesis compartment via one of the microfluidic channels 68a,b, and configured to comprise solutions of memory nucleotides 24. The controller 64 is configured to repeatedly perform: receiving a sub-sequence of the sequence of bits, the sub-sequence comprising at least one bit; selecting memory nucleotides 24 based on the sub-sequence; forwarding a solution comprising the selected memory nucleotides 24 via one of the microfluidic channels 68a,b to the memory DNA 32 synthesis compartment 66, thereby providing contact between the selected memory nucleotides 24 and the enzyme 28; and synthesising a portion 30 of memory DNA 32 from a portion of the strand 20 of memory writing substrate DNA 22 by the enzyme and at least one of the memory nucleotides 24 of the solution, thereby producing memory DNA 32 comprising memory nucleotides 24 corresponding to bits of the sequence of bits.

The microfluidic channels 68a,b may each be directly connected to the compartment 66, or may be indirectly connected via an additional channel. The memory nucleotide compartments 70a,b may alternatively be arranged of the chip.

The controller may be arranged for receiving of data, such as by, for example, being connected to a data storing or producing unit. The controller being configured to repeatedly perform selecting memory nucleotides 24 based on the received at least one bit, may be for example by selecting one type of memory nucleotides 24 if the received sub-sequence comprises a predetermined sequence of bit-values, for example 0; 1; 0,1; 1,0; 0,0; 1,1; or 0,0,0. Further, the controller may be configured to keep track of bases of the portion of the memory writing substrate DNA, for example by keeping track of advancement of the synthesising, thereby selecting a type of memory nucleotide to base pair with the bases of the portion of the memory writing substrate DNA.

The forwarding the solution comprising the selected memory nucleotides 24 via one of the microfluidic channels 68a,b to the memory DNA 32 synthesis compartment 66 may be, for example, by controlling a flow generator, such as a pump, arranged to pump the solution.

The microfluidic chip may further comprise, or be arranged to be connected to, compartments arranged for comprising buffers, electrolytes or ion-solutions, fluidically connected to the DNA synthesis compartment via microfluidic channels.

The microfluidic chip may further comprise an array of a plurality of memory writing substrate DNA, arranged in the DNA synthesis compartment, or distributed in a plurality of DNA synthesis compartments.

The micro-fluidic system 60 may be for performing the method according to the first aspect. The microfluidic system 60 may be for writing data in form of DNA, the data comprising a sequence of bits, by in-vitro enzymatically producing memory DNA 32 from a strand of memory writing substrate DNA 22.

Further disclosed is memory DNA 32 comprising a sequence of memory nucleotides 24 corresponding to a sequence of bits.

In the above the inventive concept has mainly been described with reference to a limited number of examples. However, as is readily appreciated by a person skilled in the art, other examples than the ones disclosed above are equally possible within the scope of the inventive concept, as defined by the appended claims.

---

---

What is claimed is:

1. A method for writing data comprising a sequence of bits, the data being written in a form of DNA, by in-vitro enzymatically producing memory DNA from a first strand of DNA having a predetermined or known sequence, the method comprising:
  repeating of:
    receiving a sub-sequence of the sequence of bits, the sub-sequence comprising at least one bit;
    selecting memory nucleotides based on the sub-sequence and for base pairing with bases of a portion of the first strand of DNA, the selecting comprising:
      selecting a memory nucleotide, comprising a first label or first modification, on a condition that the sub-sequence comprises a predetermined first sequence of bit-values, or
      selecting a memory nucleotide, comprising a second label or second modification, on a condition that the sub-sequence comprises a predetermined second sequence of bit-values;
    contacting, in liquid medium comprising the first strand of DNA contacted with an enzyme, the selected memory nucleotides and the enzyme; and
    synthesising a portion of the memory DNA from the portion of the first strand of DNA by the enzyme and at least one of the memory nucleotides of the solution,
  thereby producing memory DNA comprising memory nucleotides corresponding to bits of the sequence of bits.

2. The method for writing data according to claim 1, wherein the first and second labels are selected from the group consisting of fluorescent dyes, functional groups, and bulky or sterically differentiating groups, wherein the functional groups are selected from the group consisting of biotin, azide-, carboxy-, thiol-, epoxy-moieties, the bulky or sterically differentiating groups are selected from polyethylene glycol units of different length, and the first or second modification is a chemical group or functionality selected from the group consisting of biotin, azide-, carboxy-, thiol-, epoxy-moieties for post-synthesising labelling of the memory nucleotide with the first or second label respectively.

3. A method for writing data comprising a sequence of bits, the data being written in a form of DNA, by in-vitro enzymatically producing memory DNA from a first strand of DNA having a predetermined or known sequence, the method comprising:
repeating of:
receiving a sub-sequence of the sequence of bits, the sub-sequence comprising at least one bit;
selecting memory nucleotides based on the sub-sequence and for base pairing with bases of a portion of the first strand of DNA;
contacting, in liquid medium comprising the first strand of DNA contacted with an enzyme, the selected memory nucleotides and the enzyme; and
synthesising a portion of the memory DNA from the portion of the first strand of DNA by the enzyme and at least one of the memory nucleotides of the solution, wherein the portion of the first strand of DNA comprises base analogues capable of pairing with more than one type of base, thereby capable of synthesising using memory nucleotides having different bases,
thereby producing memory DNA comprising memory nucleotides corresponding to bits of the sequence of bits.

4. The method for writing data according to claim 3, wherein the memory nucleotides are selected from nucleotides comprising base A or base C, and the portion of the first strand of DNA comprises an 8-oxodG or inosine group.

5. The method according to claim 4, wherein the selecting of memory nucleotides comprises selecting base A on a condition that the sub-sequence comprises a predetermined first sequence of bit-values; and selecting base C on a condition that the sub-sequence comprises a predetermined second bit-sequence.

6. The method according to claim 1, further comprising, after the synthesizing, halting the synthesizing.

7. The method according to claim 3, wherein the portion of the first strand of DNA comprises cleavable chain terminators or reversible nucleic acid binders, wherein the halting the synthesising is realised by the cleavable chain terminators or reversible nucleic acid binders, and the method further comprising, prior to the synthesising:
cleaving the cleavable chain terminator, or unbinding of the reversible nucleic acid binders, thereby allowing initiating synthesising.

8. The method according to claim 6, wherein the halting the synthesising is realised by deactivation of the enzyme by adjusting synthesis conditions in vicinity of the portion of the first strand of DNA, preferably by adjusting ion concentration and/or temperature, thereby halting or slowing down the synthesis and the method further comprising, prior to the synthesising, activating the enzyme by adjusting synthesis conditions in vicinity of the portion of the first strand of DNA, by adjusting ion concentration and/or by adjusting temperature, thereby initiating synthesising.

9. The method according to claim 6, wherein the halting the synthesizing is realized by the next downstream base on the first strand of DNA not being compatible with the base of the selected memory nucleotide.

10. The method for writing data according to claim 3, wherein the enzyme is selected from the group consisting of polymerases, reverse transcriptases, and RNA polymerases.

11. The method for writing data according to claim 1, wherein the first strand of DNA is present together with a complementary strand of DNA.

12. The method for writing data according to claim 1, wherein produced memory DNA comprises a strand of DNA having memory nucleotides corresponding to and having the same sequence as the data comprising the sequence of bits.

13. A micro-fluidic system comprising a microfluidic chip and a controller, wherein the microfluidic chip comprises:
a memory DNA synthesis compartment configured to comprise a first strand of DNA contacted with an enzyme in liquid,
microfluidic channels fluidically connected with the memory DNA synthesis compartment and configured to forward liquids to the memory DNA synthesis compartment,
memory nucleotide compartments, each fluidically connected to the memory DNA synthesis compartment via one of the microfluidic channels, and configured to comprise a solution of memory nucleotides,
and wherein the controller is configured to repeatedly perform:
receiving a sub-sequence of the sequence of bits, the sub-sequence comprising at least one bit;
selecting memory nucleotides based on the sub-sequence, the selecting comprising:
selecting a memory nucleotide comprising a first label or first modification, on a condition that the sub-sequence comprises a predetermined first sequence of bit-values, or
selecting a memory nucleotide comprising a second label or second modification, on a condition that the sub-sequence comprises a predetermined second sequence of bit-values;
forwarding a solution comprising the selected memory nucleotides via one of the microfluidic channels to the memory DNA synthesis compartment, thereby providing contact between the selected memory nucleotides and the enzyme; and
synthesising a portion of memory DNA from a portion of the first strand of DNA by the enzyme and at least one of the selected memory nucleotides of the solution,
thereby producing memory DNA comprising memory nucleotides corresponding to bits of the sequence of bits.

14. A micro-fluidic system comprising a microfluidic chip and a controller, wherein the microfluidic chip comprises:
a memory DNA synthesis compartment configured to comprise a first strand of DNA contacted with an enzyme in liquid,
microfluidic channels fluidically connected with the memory DNA synthesis compartment and configured to forward liquids to the memory DNA synthesis compartment,
memory nucleotide compartments, each fluidically connected to the memory DNA synthesis compartment via one of the microfluidic channels, and configured to comprise a solution of memory nucleotides, and wherein the controller is configured to repeatedly perform:
- receiving a sub-sequence of the sequence of bits, the sub-sequence comprising at least one bit;
- selecting memory nucleotides based on the sub-sequence;
- forwarding a solution comprising the selected memory nucleotides via one of the microfluidic channels to the memory DNA synthesis compartment, thereby providing contact between the selected memory nucleotides and the enzyme; and
- synthesising a portion of memory DNA from a portion of the first strand of DNA by the enzyme and at least one of the selected memory nucleotides of the solution, wherein the portion of the first strand of DNA comprises base analogues capable of pairing with more than one type of base, thereby capable of synthesising using memory nucleotides having different bases,
- thereby producing memory DNA comprising memory nucleotides corresponding to bits of the sequence of bits.

* * * * *

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Example of strand of memory writing substrate
      DNA

<400> SEQUENCE: 1
cacacatggg cacacatggg cacacatggg                                    30